(12) United States Patent
Zuppiger

(10) Patent No.: US 9,448,248 B2
(45) Date of Patent: Sep. 20, 2016

(54) METHOD AND SYSTEM FOR FLUID SURFACE DETECTION

(71) Applicant: Roche Molecular Systems, Inc., Pleasanton, CA (US)

(72) Inventor: Adelrich Zuppiger, Siebnen (CH)

(73) Assignee: Roche Molecular Systems, Inc., Pleasanton, CA (US)

(*) Notice: Subject to any disclaimer, the term of this patent is extended or adjusted under 35 U.S.C. 154(b) by 266 days.

(21) Appl. No.: 14/092,099

(22) Filed: Nov. 27, 2013

(65) Prior Publication Data
US 2014/0152326 A1    Jun. 5, 2014

(30) Foreign Application Priority Data

Dec. 4, 2012 (EP) .................................... 12195422

(51) Int. Cl.
| | | |
|---|---|---|
| *G01N 27/22* | (2006.01) | |
| *G01N 35/10* | (2006.01) | |
| *G01F 23/26* | (2006.01) | |

(52) U.S. Cl.
CPC .......... *G01N 35/1011* (2013.01); *G01F 23/266* (2013.01); *G01F 23/268* (2013.01); *G01N 35/1065* (2013.01); *G01N 2035/1025* (2013.01); *G01N 2035/1076* (2013.01)

(58) Field of Classification Search
CPC ... G01N 27/22; G01F 23/266; G01F 23/268; G01R 27/2605
USPC ................................. 324/663, 664, 667, 671
See application file for complete search history.

(56) References Cited

U.S. PATENT DOCUMENTS

| | | | |
|---|---|---|---|
| 4,818,492 A | | 4/1989 | Shimizu |
| 5,049,826 A | | 9/1991 | Sasao |
| 5,304,347 A | * | 4/1994 | Mann .................... G01F 23/263 422/50 |
| 5,365,783 A | * | 11/1994 | Zweifel ................. G01F 23/266 324/662 |
| 5,648,727 A | | 7/1997 | Tyberg et al. |
| 5,843,378 A | | 12/1998 | El-Hage et al. |

(Continued)

FOREIGN PATENT DOCUMENTS

| | | |
|---|---|---|
| CH | 702427 A1 | 6/2011 |
| DE | 19756842 A1 | 5/1999 |

(Continued)

*Primary Examiner* — Arleen M Vazquez
*Assistant Examiner* — Robert P Alejnikov, Jr.
(74) *Attorney, Agent, or Firm* — Pamela C. Ancona; David J. Chang

(57) ABSTRACT

The present invention pertains to a method for detecting a fluid surface, comprising the following steps: providing at least one probe having an electric capacitance with respect to its surroundings; moving the probe into or out of a fluid; charging the probe by applying a periodic first electric signal to the probe for activating the probe; applying a periodic third electric signal to one or more electrically conductive regions different from the probe simultaneously with applying the first electric signal to the probe, wherein the third electric signal corresponds to the first electric signal or an amplified/damped first electric signal; at least partially discharging the probe so as to obtain a discharging current; detecting a second electric signal based on the discharging current; analyzing the second electric signal or a signal derived from the second electric signal with respect to the capacitance of the probe; identifying the fluid surface of the fluid based on a change of the capacitance of the probe. It further relates to a corresponding system adapted to perform the method.

15 Claims, 6 Drawing Sheets

(56) References Cited

U.S. PATENT DOCUMENTS

| | | |
|---|---|---|
| 7,150,190 B2 | 12/2006 | Krufka et al. |
| 7,387,023 B2 | 6/2008 | Harazin et al. |
| 2002/0097056 A1* | 7/2002 | Blades .............. G01R 1/06788 324/536 |
| 2005/0092080 A1 | 5/2005 | Harazin et al. |
| 2009/0320567 A1* | 12/2009 | Takahashi ......... G01N 33/2858 73/53.07 |
| 2010/0332170 A1* | 12/2010 | Gao .................... G01N 27/228 702/65 |
| 2011/0264006 A1* | 10/2011 | Ali ................... A61M 5/14212 600/587 |

FOREIGN PATENT DOCUMENTS

| | | |
|---|---|---|
| EP | 0355791 B1 | 11/1994 |
| EP | 0555710 B1 | 5/2000 |
| WO | 9812513 A1 | 3/1998 |
| WO | 0019211 A1 | 4/2000 |

* cited by examiner

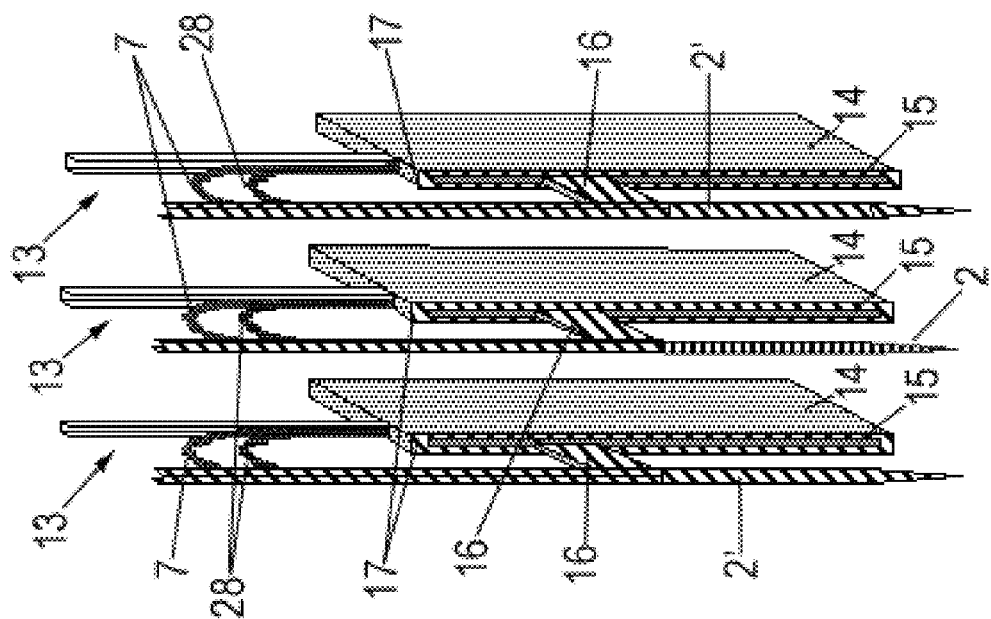
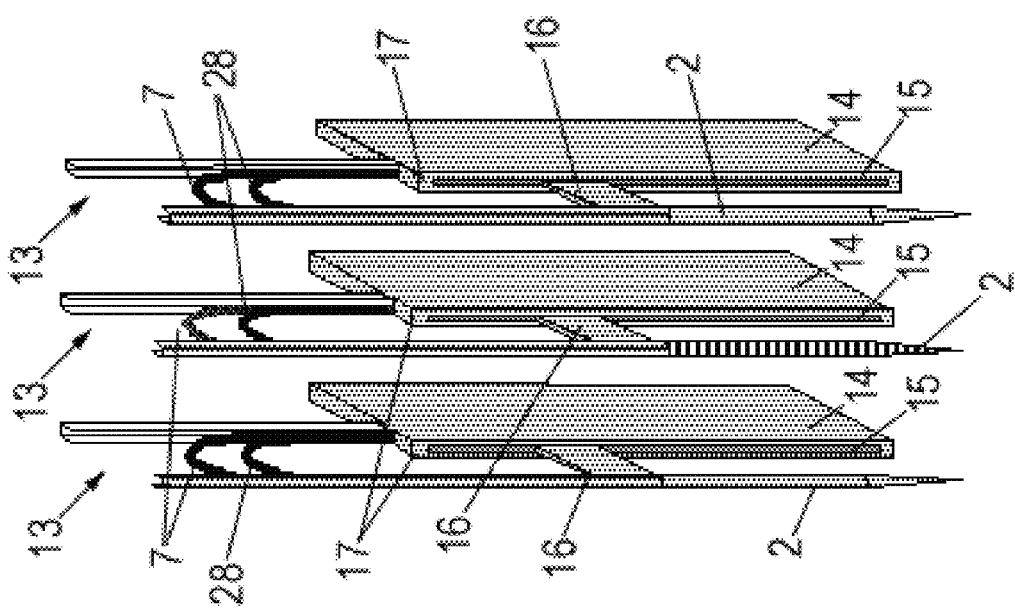
FIG. 4A
FIG. 4B

METHOD AND SYSTEM FOR FLUID SURFACE DETECTION

REFERENCE TO RELATED APPLICATIONS

This application claims priority to and benefit under 35 U.S.C. §119(a) of European Patent Application Number EP 12195422.6, filed on Dec. 4, 2012, which is hereby incorporated by reference in its entirety.

TECHNICAL FIELD

The present invention is in the field of analytical sample processing and relates to a method and an automated system for detecting a fluid surface.

BACKGROUND OF THE INVENTION

In modern clinical analyzers fluids such as bodily fluids can be tested by various clinical chemical and immunochemical methods. Many analytical methods require precise pipetting operations so as to attain satisfactory analytical accuracy. Usually, pump-controlled probes are used for aspirating and discharging fluids.

For performing pipetting operations, the probe tip must reliably be placed in the fluid. In terms of minimizing the danger of cross-contamination and facilitating probe cleaning, it often is desirable to position the probe tip just below the fluid surface. Generally, when adding or removing fluid, the probe tip can either be kept stationary with respect to the sample vessel or can be lifted or lowered so as to keep it in a dedicated position relative to the fluid surface within the fluid.

However, in many cases, fluid surfaces are not exactly known or can greatly vary from one sample vessel to another. Therefore it is necessary to detect the fluid surface in order to accurately position the probe before starting a pipetting operation.

Generally, the detection of fluid surfaces can be based on various physical principles. One method is to detect light beams directed towards and reflected from the fluid surface. By detecting the time of travel, the distance between the probe tip and the fluid surface can be calculated.

Another method frequently used in sample processing is based on detecting a characteristic change of an electrical property of the probe when the probe is brought in or out of physical contact with the fluid. Specifically, one known technique detects the change of the electric resistance of the probe when the probe tip dips into the fluid. However, in order to obtain reliable results, the fluid should be in galvanic contact with electric ground which often is not the case and therefore this technique cannot be satisfactorily used in many cases. Fluid surface detection using resistance changes of the probe is described for example in U.S. Pat. No. 5,843,378A.

Another technique is based on the application of high-frequency voltage signals to the probe which, e.g., are in a range of from 1 MHz to 1 GHz so as to generate electric impedances sensitive for surface detection. However, fluid surface detection based on high-frequent impedance measurements requires sophisticated technical equipment and is rather cost-intensive. Due to the specific operating conditions, this technique is not appropriate for use in clinical analyzers. Furthermore, electric interference effects can result in a low electromagnetic compatibility of the analyzer. Fluid surface detection based on high-frequency impedance measurements, is described for example in WO 2000019211 A1, U.S. Pat. No. 5,049,826 A, U.S. Pat. No. 5,365,783 and U.S. Pat. No. 4,818,492A.

Yet another technique is based on a change of the electric capacitance of the probe when the probe is brought in or out of physical contact with the fluid. For this purpose, the probe is repeatedly charged by periodic electric signals, with the capacitance of the probe being measured by analyzing the discharging current. Typically, low-frequent voltage signals, lower than 1 kHz, are used to avoid electric impedances. In the patent literature, fluid surface detection based on a capacitance change, is described for example in EP 89115464 A2 and U.S. Pat. No. 7,150,190 B2.

Using the capacitance technique, a change of the capacitance of the probe can be observed when the probe hits the fluid surface. However, depending on various parameters such as sample volume (in clinical analyzers, samples typically have volumes of a few Milliliters (mL) orless), design and material of the sample vessel containing the sample and the surrounding conditions thereof, the change of the electric capacitance is very small. Typically, the change of capacitance of the probe is some ten Femtofarads ($10^{-15}$ F) or less. Moreover, the measurement is likely to be disturbed by external influences such as static electric capacities with respect to adjacent probes and/or other electrically conductive parts neighbouring the probe. Further disturbances can be caused by dynamic electric capacities usually arising between moving electrically conductive components. Accordingly, when moving the probe, in particular, in a quick or irregular manner relative to electrically conductive parts, such as metallic components, dynamic electric capacities can be generated. As a matter of fact, such static and/or dynamic parasitic effects can be in the order of Picofarads ($10^{-12}$ F) which is much larger than the capacitance change of the probe caused by bringing the probe in or out of physical contact with the fluid. Hence, fluid surface detection in clinical analyzers based on a capacitance change of a probe may not yield reliable results.

Therefore, it is desirable to improve conventional systems and methods for detecting the fluid surfaces of samples which are based on a change of the electric capacitance of probes when being brought in or out of physical contact with fluids.

SUMMARY OF THE INVENTION

According to the present disclosure, a method for detecting a fluid surface is presented. The method comprises the steps of providing at least one probe having an electric capacitance with respect to its surroundings; moving the probe into or out of a fluid; charging the probe by applying a periodic first electric signal to the probe for activating the probe; applying a periodic third electric signal to one or more electrically conductive regions separate from the probe simultaneously with applying the first electric signal to the probe, wherein the third electric signal is based on the first electric signal; at least partially discharging the probe so as to obtain a discharging current; detecting a second electric signal based on the discharging current; analyzing the second electric signal or a signal derived from the second electric signal with respect to the capacitance of the probe; identifying the fluid surface of the fluid based on a change of the capacitance of the probe.

According to the present disclosure, an automated system for detecting a fluid surface of fluid contained in a fluid vessel is presented. The system comprises at least one probe having an electric capacitance with respect to its surroundings; a moving mechanism, adapted for moving the probe relative to fluid; an electric circuitry, comprising: a signal generating circuit connected to the probe, configured to generate and apply a first electric signal to the probe for charging the probe so as to obtain an activated probe, an electric drain for discharging the activated probe to generate a discharging current, a controllable switch, adapted to alternatively connect the probe to the signal generating circuit or to the electric drain; a signal detecting circuit connected to the probe, configured to detect a second electric signal based on the discharging current of the probe, a shield signal circuit, adapted to apply a third electric signal being based on the first electric signal to one or more electrically conductive regions separate from the probe; and a controller, set up to control detection of the fluid surface.

Accordingly, it is a feature of the embodiments of the present disclosure to provide an improved method and an automated system for detecting a fluid surface. Other features of the embodiments of the present disclosure will be apparent in light of the description of the disclosure embodied herein.

BRIEF DESCRIPTION OF THE DRAWINGS

Other and further objects, features and advantages of the invention will appear more fully from the following description. The accompanying drawings, which are incorporated in and constitute a part of the specification, illustrate embodiments of the invention, and together with the detailed description given below, serve to explain the principles of the invention.

FIGS. 4A-4B depict a serial arrangement of probes of the system of FIG. 1 without (FIG. 4A) and with (FIG. 4B) application of an electric shield signal;

DETAILED DESCRIPTION OF THE INVENTION

Figure 1:
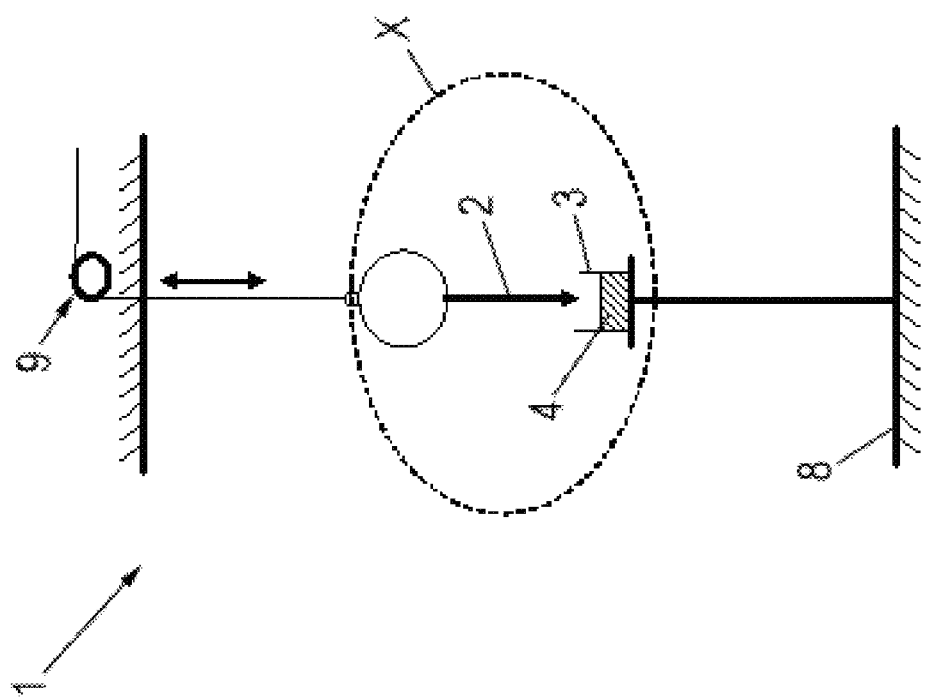
FIG. 1 is a schematic diagram of an exemplary system for detecting fluid surfaces.

According to a first aspect of the invention, a new method for detecting the surface of a fluid contained in a fluid vessel is proposed. The method will particularly be useful in connection with clinical analyzers for analyzing fluids.

The term "fluid", as used herein, can, e.g., refer to material suspected of containing an analyte of interest. The fluid can be derived from any biological source, such as a physiological fluid, including, blood, saliva, ocular lens fluid, cerebral spinal fluid, sweat, urine, milk, ascites fluid, mucous, synovial fluid, peritoneal fluid, amniotic fluid, tissue, cells or the like.

The fluid can be pre-treated prior to use, such as preparing plasma from blood, diluting viscous fluids, lysis or the like wherein methods of treatment can involve filtration, distillation, concentration, inactivation of interfering components, and the addition of reagents. A fluid may be used directly as obtained from the source or following a pre-treatment to modify the character of the fluid, e.g. after being diluted with another solution or after having been mixed with reagents e.g. to carry out one or more diagnostic assays like e.g. clinical chemistry assays, immunoassays, coagulation assays, nucleic acid testing.

According to the invention, the method for detecting a fluid surface includes a step of providing at least one probe (one or more probes) having an electric capacitance with respect to its surroundings, e.g. given by electric ground.

The method includes a further step of moving the probe into or out of the fluid and charging the probe by applying a periodic first electric signal S1 to the probe for activating the probe for fluid surface detection. In one embodiment, the first electric signal has a frequency in a range of from 1 kHz to 1 MHz.

As used herein, the term "activating" or "activated" is used for the purpose of reference only and relates to a probe which the first electric signal is applied to and which is used for fluid surface detection. Accordingly, a non-activated probe is a probe which is not used for fluid surface detection.

The method further includes a step of applying a periodic third electric signal S3 to one or more electrically conductive regions different from the activated probe simultaneously with applying the first electric signal S1 to the activated probe. The third electric signal S3 is based on the first electric signal S1. In one embodiment, the frequency of the third electric signal S3 is equal to the frequency of the first electric signal S1. In one embodiment, periodic signal pulses of the third electric signal S3 are equal to periodic signal pulses of the first electric signal S1. In one embodiment, the third electric signal S3 corresponds to (is equal to) the first electric signal or corresponds to an amplified/damped first electric signal S1. In one embodiment, the third electric signal S3 is derived from the first electric signal S1. In one embodiment, the third electric signal S3 is the first electric signal S1.

The method further includes a step of at least partially discharging the activated probe so as to obtain a discharging current and a step of detecting a second electric signal S2 based on the discharging current. In one embodiment, the first electric signal S1 is derived from the second electric signal S2.

The method further includes a step of analyzing the second electric signal S2 or a signal derived from the second electric signal S2 with respect to the capacitance of the activated probe and a step of identifying the fluid surface based on a change of the capacitance of the activated probe.

Accordingly, by applying the third electric signal S3 to electrically conductive regions which can influence the capacitance of the activated probe, the activated probe can efficiently be shielded from disturbances influencing the fluid surface detection. The third electric signal S3 thus acts as a "shield signal".

In one embodiment comprising a plurality of probes, e.g. in a serial arrangement, the third electric signal S3 is applied to one or more non-activated probes arranged adjacent to the activated probe. Specifically, the third electric signal S3 can be applied to all non-activated probes arranged adjacent to (e.g. on one or both sides of) the activated probe. Since non-activated probes neighbouring the activated probe frequently are a major cause for disturbances, the reliability of the fluid surface detection can be strongly improved.

In one embodiment, the third electric signal S3 is applied to one or more components of a moving system for moving the activated probe and/or one or more components of the moving system for moving one or more non-activated probes arranged adjacent to the activated probe. Components of the moving system often have large electrically conductive areas which can strongly influence the capacitance of the activated probe, especially when the activated probe is moved with respect to these areas. Accordingly, by shielding these areas, the reliability of the fluid surface detection can be strongly improved.

In one embodiment, the third electric signal S3 is applied to system fluid of the activated probe and/or to system fluid(s) of one or more non-activated probes arranged adjacent to the activated probe. The system fluid is being used for operating the probes as pipettes. System fluid can also be a major cause of disturbances to the fluid surface detection so that the reliability of the fluid surface detection can be strongly improved.

In one embodiment, the third electric signal S3 is applied to a coaxial line of the activated probe and/or to coaxial line(s) of one or more non-activated probes arranged adjacent to the activated probe. Coaxial lines can also be a major cause for disturbances to fluid surface detection, especially when the activated probe is moved and/or when the coaxial lines are moved in non-controlled manner (generation of dynamic capacitances). Accordingly, by shielding coaxial lines, the reliability of the fluid surface detection can be strongly improved.

In one embodiment, the first electric signal S1 is modulated by a fourth electric signal which periodically applies the first electric signal S1 to the probe. Specifically, in the case of using a plurality of probes, e.g., in a serial arrangement with respect to each other, the probes can be sequentially activated one after the other to further improve the reliability of fluid surface detection.

According to a second aspect of the invention, a new automated system for detecting a fluid surface of fluid contained in a fluid vessel is disclosed. The system can be configured in various ways in accordance with specific demands of the user and, e.g., can be part of an automated clinical analyzer related to various analyses such as, but not limited to, clinical-chemical, biochemical, or immunochemical analyses.

According to the invention, the system includes at least one probe, adapted to be positioned with respect to the fluid. Due to the capacitive coupling to the surroundings, e.g. electric ground, the probe has an electric capacitance.

The system further includes a moving mechanism, adapted for positioning the probe relative to the fluid, e.g., for moving the probe into and out of the fluid. In one embodiment, the probe preferably is made of or at least comprises an electrically conductive material.

The system further includes an electric circuitry, comprising a signal generating circuit connected to the probe and configured to generate and apply a first electric signal S1 to the probe for charging the probe so as to obtain an activated probe. The circuitry further comprises an electric drain such as, but not limited to, electric ground, for discharging the activated probe to generate a discharging current and a controllable switch, adapted to alternatively connect the probe to the signal generating circuit or to drain. The circuitry further comprises a signal detecting circuit connected to the probe, configured to detect a second electric signal S2 based on the discharging current of the probe. The circuitry further comprises a shield signal circuit, adapted to apply a third electric signal S3 based on the first electric signal S1 to one or more electrically conductive regions different from the probe.

The system further includes a controller, set up to control detection of the fluid surface.

With respect to the first, second and third electric signal, reference is made to explanations above in connection with the method of the invention.

In one embodiment, the controller is set up to move the probe into the fluid, to control the switch to repeatedly charge and at least partially discharge the probe by means of the first electric signal S1, to control the electric circuitry to detect the second electric signal, to analyze the second electric signal S2 or a signal derived from the second electric signal S2 with respect to the capacitance of the activated probe, and to identify the fluid surface based on a change of the capacitance of the probe, wherein the third electric signal S3 is applied to the one or more electrically conductive regions separate from the probe simultaneously with applying the first electric signal S1 to the probe.

In one embodiment, the shield signal circuit is electrically connected to one or more of the following electrically conductive regions:
  one or more non-activated probes arranged adjacent to the activated probe,
  one or more components of the moving system for moving the activated probe and/or one or more components of the moving system for moving one or more non-activated probes arranged adjacent to the activated probe,
  system fluid of the activated probe and/or system fluid of one or more non-activated probes arranged adjacent to the activated probe,
  a coaxial line of the activated probe and/or a coaxial line of one or more non-activated probes arranged adjacent to the activated probe.

In one embodiment, the signal generating circuit is configured as an oscillator comprising a Schmitt trigger circuit connected to a resistance-capacitance circuit (resistance serially connected to capacitance), with the capacitance being provided by the activated probe.

In one embodiment, the probe(s) is/are configured to perform pipetting operations for pipetting fluids so as to withdraw or discharge fluids when generating a negative or positive pressure therein. The probe thus has a double functionality of detecting a fluid surface and pipetting fluid. Hence, pipetting operations can be combined with an exact positioning of the probe within the fluid. The probe for pipetting fluids can, e.g., be embodied as needle made of metallic material such as, but not limited to, a steel needle.

In one embodiment, the fluid vessel comprises a vessel portion made of an electrically conductive material, wherein the conductive vessel portion is being supported by an electrically conductive support, such as but not limited to, an electrically conductive work-plate, in electric contact therewith. As a result, the capacitive coupling between the probe and the surroundings can be improved.

The system of the invention thus allows for a robust detection of a fluid surface by applying an electric shield signal to regions which are likely to influence the capacitance of the activated probe and, thus, can disturb the fluid surface detection. The system can be used to perform the above-described method of the invention.

A major advantage of the invention is given by the fact that, in contrast to the prior art techniques, by electrically shielding disturbances from the surroundings by applying the third electric signal S3, the electric capacitance of the activated probe can reliably be used to detect the fluid surface.

The above-described various embodiments of the system and method of the invention can be used alone or in any combination thereof without departing from the scope of the invention.

By way of illustration, specific exemplary embodiments in which the invention may be practiced now are described. First referring to FIGS. 1 to 3, by means of schematic diagrams, an automated system for detecting a fluid surface is explained. The system will be particularly useful in connection with clinical analyzers for analyzing fluid samples.

Figure 2:
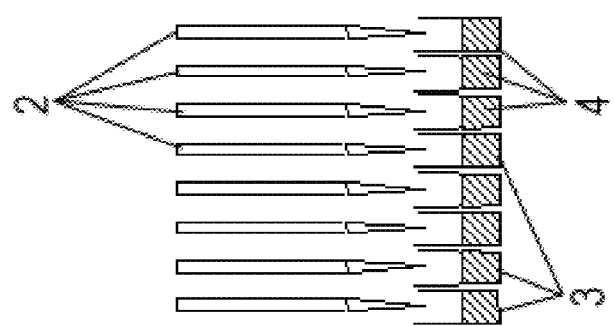
FIG. 2 depicts a serial arrangement of probes.
Figure 3:
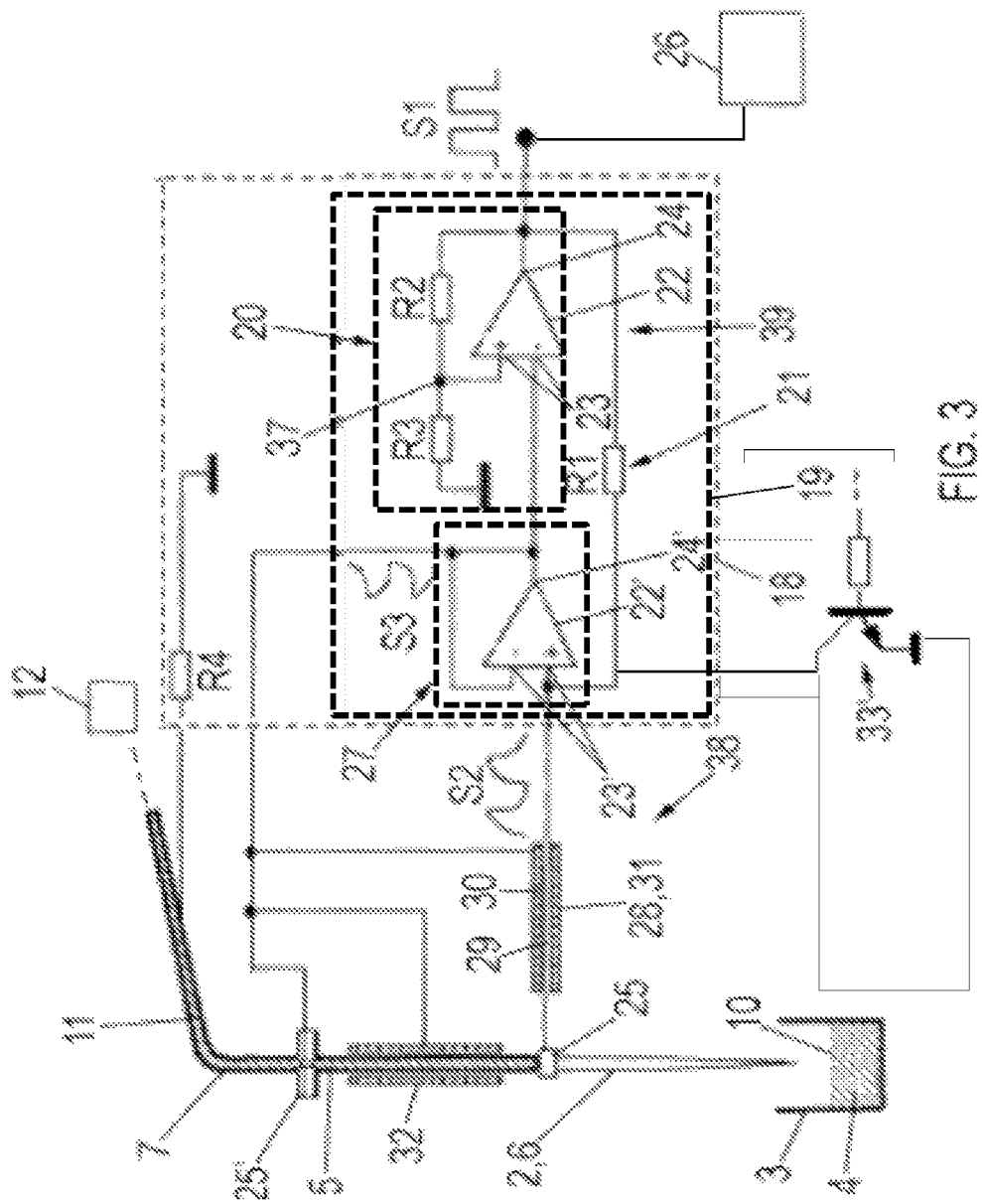
FIG. 3 depicts detail X of the system of FIG. 1.

Specifically, FIG. 1 illustrates the general concept of an exemplary system for detecting a fluid surface. FIG. 2 depicts a serial arrangement of probes for use in the system of FIG. 1. FIG. 3 depicts detail "X" of FIG. 1 comprising an electric circuitry for detecting fluid surfaces.

With particular reference to FIG. 1, the system generally referred to as reference numeral 1 includes at least one probe 2 for detecting the fluid surface of a fluid 4 contained in a fluid vessel 3, e.g., arranged below the probe 2. In one embodiment, the probe 2 is configured as pipette, adapted for performing pipetting operations, i.e., for aspirating and dispensing fluids. Specifically, the probe 2 is provided with an inner (fluid) channel 5 which at probe tip 6 opens to the surroundings.

As illustrated in FIG. 3, at an opposite side of the probe tip 6, each probe 2 is connected by fluid to a pump 12 by a pump conduit 7 for generating a negative or positive pressure in the fluid channel 5 so that fluid can be sucked in or discharged from the probe 2 according to the specific demands of the user. Since pumps for operating pipettes are well-known to those of skill in the art, e.g. from commercially available analyzers, it is not necessary to further elucidate the pump 12 herein. As illustrated in FIG. 3, the pump conduit 7 is connected to electric ground via resistance R4.

With continued reference to FIG. 3, in one embodiment, the pump conduit 7 is filled with liquid system fluid 11 which can be moved back and forth by operating the pump 12. The system fluid 11 can also be discharged through the probe tip 6, e.g., for cleaning the fluid channel 5 of the probe 2.

In one embodiment, the probe 2 is configured as a needle made of metallic material such as, but not limited to, stainless steel. Specifically, the probe 2 can have a sharpened probe tip 6 for facilitating penetration of a cap (not illustrated) in case of a top-closed fluid vessel 3.

As illustrated in FIG. 2, in one embodiment, the system 1 comprises a plurality of probes 2 serially arranged with respect to each other. Accordingly, fluid surfaces of a corresponding number of fluids 4 contained in fluid vessels 3 arranged side-by-side can be detected simultaneously or sequentially without lateral movements of the probes 2. While a number of eight probes 2 is shown for the purpose of illustration only, those of skill in the art will appreciate that more or less probes 2 can be envisaged according to the specific demands of the user. It is indicated that eight probes 2 can be used as standard configuration in many applications.

As detailed above, each probe 2 has a double functionality of detecting fluid surfaces and aspirating or dispensing fluids. For moving and positioning one or more probes 2 with respect to fluids 4 contained in fluid vessels 3, the system 1 includes an automated moving mechanism 9. Specifically, in one embodiment, the moving mechanism 9 is configured to vertically move the probes 2 as illustrated by the double-headed arrow. Usually, the fluid vessels 3 containing the fluids 4 are kept stationary while moving the probes 2 for detecting the fluid surfaces thereof.

With particular reference to FIGS. 4A and 4B, in one embodiment, the moving mechanism 9 includes plural transfer heads 13 serially arranged with respect to each other. Each transfer head 13 comprises a parallelepiped-shaped transfer block 14 having a face-side 17 provided with a vertically oriented block opening 15 for receiving by sliding a plate-like probe holder 16 configured for fixing one probe 2. The probe holder 16 is operatively coupled to a drive mechanism (not illustrated) such as a spindle drive so that the probe holder 16 can be moved in vertical direction along the block opening 15. Hence, the probe 2 fixed to the probe holder 16 can be vertically moved towards and away from fluid 4 contained in a fluid vessel 3 below the probe 2. Since each probe 2 is attached to an individual transfer head 13, the probes 2 can be moved independently from each other. Alternatively, more than one probe 2 can be fixed to one probe holder 16 so as to be moved together when moving the probe holder 16. In FIGS. 4A and 4B a number of three transfer heads 13 is illustrated for the purpose of illustration only. It is indicated that any other number of transfer heads 13 can be envisaged according to the specific demands of the user, e.g., eight transfer heads 13, each of which being provided with one probe 2 corresponding to the arrangement of FIG. 2.

In one embodiment, the transfer heads 13 are fixed to a carriage (not illustrated) movable in two directions of travel over the horizontal work-plate 8, e.g., based on a translating mechanism (not illustrated) having two rails arranged in orthogonal relationship with respect to each other. Accordingly, each probe 2 can be moved in lateral and/or vertical directions. Since such carriage and translating mechanism are well-known to the skilled persons, e.g., from commercially available analyzers, they are not further elucidated herein.

Accordingly, by operating the moving mechanism 9, each probe 2 can be lowered so as to have a position where the probe tip 6 dips into the fluid 4 contained in a fluid vessel 3 below the probe 2. The probe tip 6 can, e.g., be positioned a small distance below the fluid surface 10 in order to minimize the contact between the fluid 4 and the probe tip 6.

As illustrated in FIG. 2, the system may contain one or more fluid vessels 3, e.g., serially arranged with respect to each other, configured for receiving any fluids 4 of interest such as bodily fluids, e.g., blood, urine or the like. The fluid vessels 3 can, e.g., be configured as tubes, vials or wells of a multi-well plate. In one embodiment, the fluid vessels 3 are made of electrically isolating material such as, but not limited to, plastics. In one alternative embodiment, the fluid vessels 3 are made of electrically conducting material such as, but not limited to, stainless steel, to improve capacitive coupling to the probe 2. In one embodiment, the fluid vessels 3 are electrically connected to electric ground. In one embodiment, the fluid vessels 3 are provided with a top cover (not illustrated) made of electrically isolating material such as, but not limited to, plastics or rubber.

In the system 1, in one embodiment, each probe 2 is made of an electrically conductive material such as, but not limited to, a metallic material like stainless steel. Accordingly, the probe 2 has an (intrinsic) electrostatic capacitance depending on the capacitive coupling of the probe 2 to the surroundings (usually electric ground), e.g., to the work-plate 8. Generally, when the probe 2 is lowered into the fluid 4, a change of the electric capacitance of the probe 2 can be observed due to the fact that the capacitance of the probe 2 is altered by the capacitance of the (electrically conductive) fluid 4. However, as already discussed in the introductory portion, in clinical analyzers, the change of the electric capacitance of the probe 2 observed by dipping the probe tip 6 into the fluid 4 typically is as small as some ten Femto-farads ($10^{-15}$ F) or even less.

With continued reference to FIG. 1, providing an ideal situation for capacitance measurements, the fluid 4 is galvanically connected to electric ground (e.g. by means of an electrically conductive fluid vessel 3) or has at least a strong capacitive coupling thereto. However, as is more in clinical analyzers, there is only a weak capacitive coupling between the fluid 4 and electric ground.

With particular reference to FIG. 3, for fluid surface detection, each probe 2 is electrically connected to an electric circuitry generally referred to as reference numeral 18. The electric circuitry 18 comprises a signal generating circuit 39, configured to generate and apply a periodically oscillating electric (voltage) signal S1 to the probe 2 for electrically charging the probe 2 as well as a signal detecting circuit 38, configured to detect a second electric signal S2 in response to the first electric signal S1 based on a discharging current of the probe 2.

Specifically, the circuitry 18 includes an oscillator 19 for generating the first electric signal S1 comprising a Schmitt trigger circuit 20 and a resistance-capacitance (integrating) circuit 24 ("RC circuit") consisting of the electric resistance R1 21 and the probe 2 (capacitance C) serially connected to the resistance R1 21.

Generally, the Schmitt trigger circuit 20 is an electric circuit having a positive feedback loop by adding a part of the output voltage to the input voltage with a loop gain greater than 1. The basic principle behind the Schmitt trigger circuit 20 is that the output voltage of the Schmitt trigger circuit 20 retains its value until the input voltage changes sufficiently to trigger a change.

As illustrated, in one embodiment, the Schmitt trigger circuit 20 is implemented by an operational amplifier 22 having two inputs 23 (non-inverting input "+" and inverting input "−") and one output 24, with the output 24 being connected to the non-inverting input 23 via a voltage divider given by the electric resistances R2 and R3. Specifically, a connecting point 37 between the resistance R2 and resistance R3 is connected to the non-inverting input 23. The voltage divider acts like an attenuator. In one embodiment, the electric resistances R2 and R3 have values R2=427 kOhm and R3=227 kOhm. The inverting input 23 of the operational amplifier 22 is connected to the probe 2 via another operational amplifier 22' (described further below) and a coupling electrode 25 coupled to the probe 2 for transmitting the electric signal S1 to the probe 2 and coupling an electric signal S2 obtained by discharging the probe 2 out of the probe 2. As usual, the operational amplifier 22 is connected to a power supply having an upper value (+V) of, e.g., 24 Volts, and a lower value (−V) of, e.g. 0 Volts.

In the Schmitt trigger circuit 20, the operational amplifier 22 acts like a bi-stable latch that switches at a different point depending on whether the voltage at the output 24 is high or low (hysteresis effect). The hysteresis effect is controlled by the relative proportion of the resistance values and the summarized resistance value of the resistances R2 and R3.

The oscillator 19 is implemented by connecting the RC circuit 24 between the output 24 and the inverting input 23 of the operational amplifier 22. The oscillating function of the oscillator 19 is obtained by the following mechanism: in case any sort of noise (thermal or electromagnetic noise) causes the output 24 to have a voltage of more than zero volts, the non-inverting input 23 is also positive which, due to the positive feedback, results in a situation that the voltage of the output 24 approaches the upper value (+V) of the power supply. Since the inverting input 23 and the output 24 are linked by the RC circuit 24, the inverting input 23 approaches the output voltage with a time constant depending on the resistance value of the electric resistance R1 21 and the capacity C of the probe 2. When the voltage at the inverting input 23 is greater than the voltage at the non-inverting input 23, the voltage of the output 24 is decreased to approach the lower value (−V) of the power supply. When the voltage of the output 24 continues to decrease, the difference between the inverting and non-inverting inputs 23 is changed resulting in a situation that the voltage of the inverting input 23 approaches the voltage of the output 24 so that the cycle repeats itself. Accordingly, the voltage of the output 24 of the operational amplifier 22 is switched between the upper and lower values (+V, −V) of the power supply when the input is above the upper threshold or below the lower threshold. Between the upper and lower thresholds, the voltage of the output 24 remains unchanged.

The electric circuitry 18 further includes a controllable switch, e.g., a transistor 33' schematically illustrated in FIG. 3, adapted to alternatively (periodically) connect the probe 2 to the output 24 of the operational amplifier 22 for charging the probe 2 by means of the first electric signal or to electric ground for discharging the probe 2. The transistor 33' can be controlled by a controller 26.

Hence, when discharging the probe 2, the second electric signal S2 based on the discharging current of the probe 2 can be obtained via the coupling electrode 25 which is transmitted to the operational amplifier 22. The output 24 of the operational amplifier 22 (oscillator 19) becomes a square-wave electric signal S1, the frequency of which very much depending on the resistance value of the resistance R1 and the electric capacity C of the probe 2 (as well as the switching points of the Schmitt trigger circuit 20). Accordingly, by varying the resistance value of the resistance R1, the frequency of the first electric signal S1 can readily be adapted to the capacity of the probe. In one embodiment, the frequency of the first electric signal S1 is in a range of from 5 kHz to 1 MHz and, e.g., has a value of 100 kHz. In one embodiment, the resistance R1 has a resistance value R1=180 kOhm.

Accordingly, the capacity C of the probe 2 can readily be determined by analyzing the first electric signal S1 obtained at the output 24 with respect to its frequency or period (time constant). As a result, a change of the capacity C of the probe 2 can also be detected.

With continued reference to FIG. 3, in the system 1, the controller 26 can be used for controlling the detection of fluid surfaces and the pipetting of fluids. Specifically, the controller 26 is set up to control moving and positioning of the probes 2, in particular, based on a detection result with respect to the respective fluid surface 10 obtained from analyzing the electric signal S1. The controller 26 may, e.g., be embodied as programmable logic device (microprocessor) running a computer-readable program provided with instructions to perform operations in accordance with a predetermined process routine. For this purpose, the controller 26 is electrically connected to the various system components which require control and/or provide information including the output 24 of the operational amplifier 22 and the moving mechanism 9 for moving and positioning the probes 2 with respect to fluids 4.

With continued reference to FIG. 3, in the system 1, the electric circuitry 18 further comprises a shield signal circuit 27 for generating and applying a third electric signal S3 ("electric shield signal") to electrically conductive regions which are likely to influence the capacitance of the probe 2 so as to disturb the fluid surface detection. Specifically, the shield signal circuit 27 comprises the operational amplifier 22' having two inputs 23' (non-inverting input "+" and inverting input "−") and one output 24'. The output 24' is connected to the inverting input 23' and to the inverting input 23 of the other operational amplifier 22. The non-inverting input 23' of the operational amplifier 22' is connected to the coupling electrode 25 via a coaxial line 28. The second electric signal S2 based on the discharging current of the probe 2 is forwarded to the inverting input 23 of the operational amplifier 22 via the operational amplifier 22'.

The output 24' of the operational amplifier 22' is connected to various system components which may cause changes of the electric capacitance C of the probe 2 for the purpose of charging these system components with the electric shield signal S3. Stated more particularly, the output 24' is electrically connected to

- a tubular conducting shield 31 surrounding an insulating layer 30 surrounding an electric conductor 29 of the coaxial line 28 of the probe 2 (and the tubular conducting shields 31 of the neighbouring probes 2 on each side of the probe 2),
- the system fluid 11 of the probe 2 via the coupling electrode 25' (and the system fluids 11 of the two neighbouring probes 2 on each side of the probe 2 via coupling electrodes 25'),
- various system components belonging to the surroundings of the probe 2 schematically illustrated in FIG. 3 at reference numeral 32.

The application of the electric shield signal S3 is further detailed in connection with FIGS. 4A and 4B illustrating three probes 2, 2' in serial arrangement, each of which being fixed to an individual transfer head 13.

Specifically, in a first situation illustrated in FIG. 4A, the middle probe 2 is activated for detecting fluid surfaces by applying the electric signal S1. The probes 2' on both sides of the middle probe 2 are non-activated probes which are not used for fluid surface detection. As has been shown by practical tests, the change of the capacitance C of the activated middle probe 2 due to bringing the probe tip 6 in or out of physical contact with fluid can be strongly disturbed by the two neighbouring non-activated probes 2' on each side of the activated probe 2 (left and right probe 2) as well as the system fluids 11, the coaxial lines 28, and components of the transfer heads 13, mainly the probe holders 16 and the face sides 17 of the transfer blocks 14 of both the activated probe 2 and the two neighbouring non-activated probes 2'. For instance, the capacitance of two adjacent probe tips 6 (volume 1000 µL, distance 9 mm) amounts to about 5 Picofarads (pF) and, thus, is very large compared to the capacitance change (some ten Femtofarads or less) of the activated middle probe 2 when being brought in or out of contact with fluid, e.g. by hitting the fluid surface.

In a second situation illustrated in FIG. 4B, in order to largely avoid such influences resulting in undesired capacitance changes of the activated middle probe 2, the electric shield signal S3 is applied to:

- the two neighbouring non-activated probes 2' (as schematically illustrated in FIG. 3 at reference numeral 32),
- the system fluids 11 contained in the pump conduits 7 of the activated probe 2 and the two neighbouring non-activated probes 2',
- the coaxial lines 28 of the activated probe 2 and the two neighbouring non-activated probes 2',
- the probe holders 16 of the activated probe 2 and the two neighbouring non-activated probes 2' (as schematically illustrated in FIG. 3 at reference numeral 32), and
- the face sides 17 of the transfer blocks 14 of the activated probe 2 and the two neighbouring non-activated probes 2' (as schematically illustrated in FIG. 3 at reference numeral 32).

Since the electric shield signal S3 corresponds to the electric signal S1 except from being amplified by the operational amplifier 22', the capacitance C of the activated middle probe 2 can efficiently be shielded from influences of the surroundings disturbing the fluid surface detection. In other words, by applying the electric shield signal S3 to components neighbouring the activated middle probe 2 as above-detailed, these components can be electrically faded out or made "invisible" with respect to detecting the fluid surface 10 by the middle probe 2 activated by applying the electric signal S1. Accordingly, fluid surfaces can be detected in an accurate and reliable manner.

Accordingly, by applying the electric shield signal S3, capacitances which otherwise would add to the capacitance of the activated middle probe 2 can be shielded so as to strongly improve the sensitivity of the fluid surface detection. Furthermore, by applying the shield signal S3 to the system fluids 11 contained in the pump conduits 7 another effect of inhibiting dissipation of electric signals to electric ground can be obtained.

Figure 5:
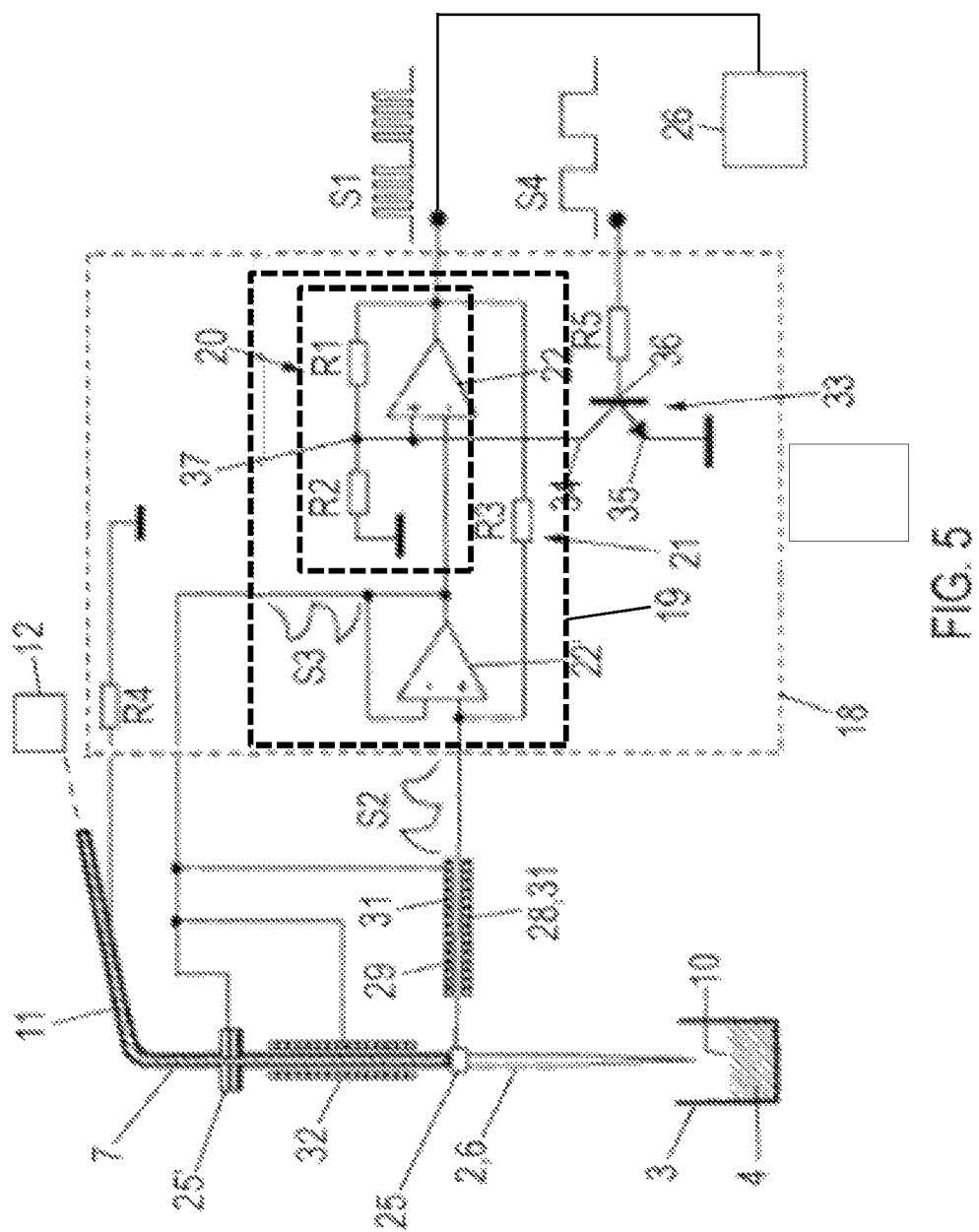
FIG. 5 depicts a variant of the system of FIG. 1.

Reference is now made to FIG. 5 depicting a variant of the exemplary system 1 of FIG. 1. In order to avoid repetitions, only the differences with respect to the system 1 of FIGS. 1 to 3 are explained and otherwise reference is made to the corresponding explanations given above.

Accordingly, the system 1 includes an electronic switch, e.g., configured as a transistor 33 such as, but not limited to, a bipolar field-effect transistor (FET). Specifically, a collector contact 34 of the transistor 33 is connected to the non-inverting input 23 of the operational amplifier 22 and an emitter contact 35 thereof is connected to electric ground. Furthermore, a base contact 36 of the transistor 33 is electrically connected to the controller 26 via resistance R5.

The controller 26 is configured to provide the base contact 36 with an electric synchronisation signal S4 having periodically repeated switching pulses such as, but not limited to, periodic square wave pulses as illustrated in FIG. 5. When applying the voltage pulses of the synchronisation signal S5 to the base contact 36, the transistor 33 can be periodically switched on or off. Stated more particularly, in the on-state, an electric path between the collector contact 34 and the emitter contact 35 is made conductive so that electric current can flow from the non-inverting input 23 of operational amplifier 22 to electric ground as indicated by the arrow. Otherwise, in the off-state, the electric path between the collector contact 34 and the emitter contact 35 is highly resistive so that the non-inverting input 23 of operational amplifier 22 is separated from electric ground.

Accordingly, by switching the transistor 33, the generation of the first electric signal S1 can be selectively blocked so as to periodically modulate the first electric signal S1 by the synchronisation signal S5.

Figure 6:
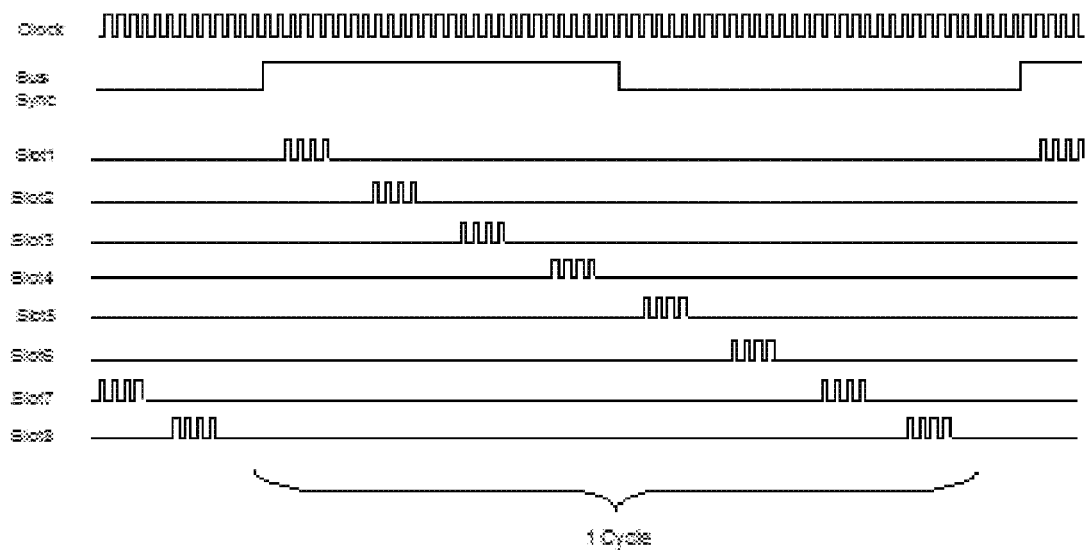
FIG. 6 is a schematic diagram illustrating the sequential activation of probes for detecting fluid surfaces.

As illustrated in FIG. 6, by applying the synchronisation signal S5 to the transistor 33, the electric signal S1 can be modulated to synchronize the activation of individual probes 2, e.g., to selectively activate individual probes 2 by charging with the first electric signal S1 and detecting the second electric signal S2 for measuring the capacitance C of the probe 2.

In one embodiment, as illustrated, eight probes 2 are sequentially (one after the other) charged with the electric signal S1 in one cycle for activation, with each cycle being periodically repeated according to the specific configuration of the synchronisation signal S5. Accordingly, each cycle contains eight time slots with each probe 2 being activated during one time slot. Accordingly, the fluid surface of fluid can be detected avoiding parasitic influences by the simultaneous measurement of other fluid surfaces.

Figure 7:
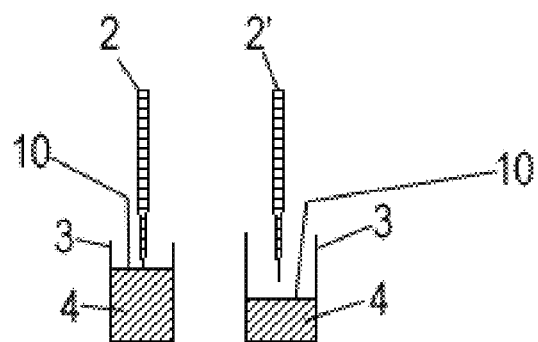
FIG. 7 is a schematic diagram illustrating a setup using probes for detecting different fluid surfaces.

Now referring to FIGS. 7 and 8A-8C, the detection of fluid surfaces is further described. As illustrated in FIG. 7, an exemplary setup of the system 1 for detecting different fluid surfaces of fluids contained in two fluid vessels 3 comprises two probes 2, 2'.

Figure 8A:
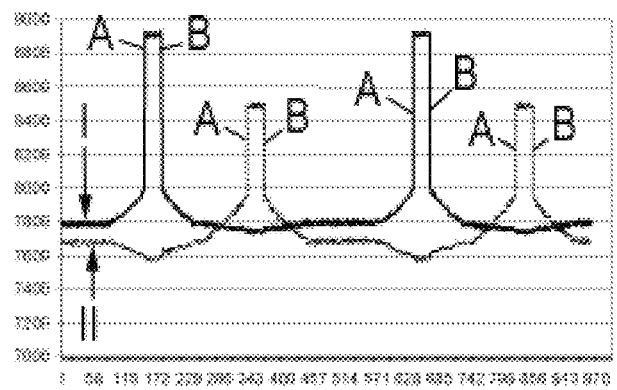
FIGS. 8A-8C are experimental results obtained with the setup of FIG. 7.

With particular reference to FIG. 8A depicting a diagram of the electric capacitance C of the two probes 2 of FIG. 7 versus time, in a first experiment, the fluid vessels 3 are spatially separated to avoid influences of the vessels to the capacitance measurements, wherein the probes 2, 2' have been individually moved into and out of the fluid 4 as well as individually activated by applying the electric signal S1. No electric shield signal S3 is applied to the non-activated probe 2'.

Specifically, curve I describes the capacitance change of the left probe 2 when being brought in and out of physical contact with the fluid 4 (while keeping the right probe 2' stationary) for detecting the higher fluid surface, and curve II the capacitance change of the right probe 2' when being brought in and out physical contact with the fluid 4 (while keeping the left probe 2 stationary) for detecting the lower fluid surface. As illustrated, when moving the left probe 2 down, a sharp increase at A of the electric capacitance C of the left probe 2 can be observed when it hits the liquid surface 10. Due to the normally large difference in electric conductivity between the air-filled free space over the fluid 4 and the electrically conductive fluid 4, the significant increase of the capacitance C is identified as fluid surface. Otherwise, when lifting the left probe 2 up, a sharp decrease at B of the electric capacitance C of left probe 2 can be observed when it leaves the fluid 4. In the diagram, the down-and-up movement of the left probe 2 is repeated once. Furthermore, when moving the right probe 2' down and up, corresponding significant changes (sharp increase at A and sharp decrease at B) of the electric capacitance C of the right probe 2 can be observed when it is brought in and out of physical contact with the fluid 4. The peak of the right probe 2' is somewhat smaller than the peak of the left probe 2 caused by the lower fluid surface. In both curves, a slight increase/decrease of the capacitance C of the probe 2, 2' when entering/leaving fluid vessel 3 can be observed. Many non-biological or biological fluids such as body fluids exhibit sufficient electric conductivity enabling detection of a significant change of the capacitance of the probe 2, 2'. Accordingly, as illustrated, the fluid surfaces can be readily detected by a significant capacitance change of the probes 2, 2'. Furthermore, the vertical position of the liquid surface 10 can be related to a predefined reference level, e.g., an upper face of the work-plate 8 the fluid vessels 3 are placed on so as to obtain a fluid level. However, in practical situations such as, but not limited to, clinical analyzers, external parasitic influences to the capacitance C of the activated probe 2, e.g. by other probes usually cannot be avoided.

Figure 8B:
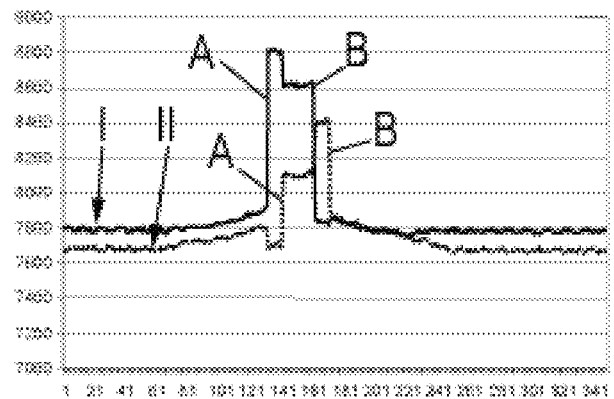

With particular reference to FIG. 8B depicting a diagram of the electric capacitance C of the two probes 2 of FIG. 7 versus time, in a second experiment, the fluid vessels 3 are close together, wherein probes 2 have sequentially (one after the other) been brought in and out of physical contact with the fluids 4. In this experiment, the electric signal S1 has only been applied to the left probe 2. Simultaneously with applying the electric signal S1, the electric shield signal S3 has been applied to the right probe 2'. The capacitances C of the left and right probes 2, 2' are detected.

Specifically, curve I describes the capacitance change of the left probe 2 when being brought in and out of physical contact with the fluid 4 for detecting the higher fluid surface, curve II the capacitance change of the right probe 2' when being brought in and out physical contact with fluid 4. Accordingly, as illustrated, when the left probe 2 moves down, a sharp increase at A of the capacitance C of the left probe 2 can be observed when the left probe 2 hits the liquid surface 10. The capacitance of the right probe 2' is slightly decreased in the moment the left probe 2 hits the liquid surface 10. When keeping the left probe 2 in the fluid 4 and moving the right probe 2' down, in the moment the right probe 2' hits the liquid surface 10 at A, the capacitance C of the left probe 2 is slightly decreased. When reversing the movement of both probes, when the left probe 2 is brought out of physical contact with the fluid 4, a sharp decrease at B of the capacitance C of the left probe 2 can be observed when the left probe 2 leaves the fluid 4. In this moment, the capacitance C of the right probe 2' is increased. Furthermore, when the right probe 2 leaves the fluid 4, a sharp decrease at B of the capacitance C of the right probe 2' can be observed.

Accordingly, the detection of the higher fluid surface by means of the activated left probe 2 can reliably be detected by a significant change (increase at A or decrease at B) of the capacitance C of the left probe 2. Disturbances from the surroundings as given by the non-activated right probe 2' decrease the capacitance C of the activated left probe 2 at A or increase the capacitance C of the activated left probe 2 at B due to applying the electric shield signal S3. Hence, since the capacitance changes of the activated left probe 2 caused by the surroundings have a different sign with respect to the capacitance changes of the left probe 2 caused by hitting or leaving the fluid surface 10, the higher fluid surface can readily be detected so as to improve the reliability of the detection.

Figure 8C:
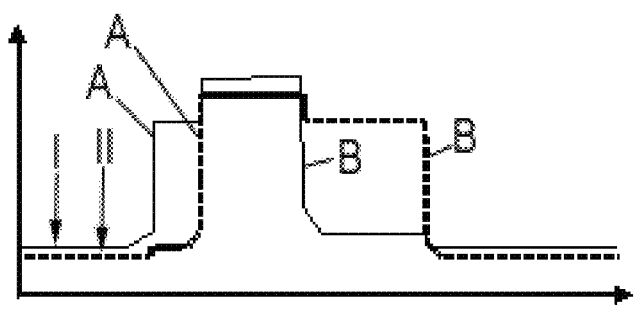

Now, with particular reference to FIG. 8C depicting a diagram of the electric capacitance of the two probes 2, 2' of FIG. 7 versus time, in a third experiment which is a variant of the second experiment the non-activated right probe 2' has been connected to electric ground instead of applying the electric shield signal S3.

Specifically, a sharp increase at A of the capacitance C of the activated left probe 2 can be observed when the left probe 2 hits the liquid surface 10. When keeping the left probe 2 in the fluid 4 and moving the right probe 2' down, in the moment the right probe 2' hits the liquid surface 10 at A, the capacitance C of the left probe 2 is further increased. When reversing the movement of both probes, when the left probe 2 is brought out of physical contact with the fluid 4, a sharp decrease at B of the capacitance C of the left probe 2 can be observed when it leaves the fluid 4. In this moment, the capacitance C of the right probe 2' is also decreased. Furthermore, when the right probe 2' leaves the fluid 4, a sharp decrease at B of the capacitance C of the right probe 2 can be observed. In this moment, also a slight decrease of the capacitance C of the left probe 2 can be observed.

Accordingly, the detection of the higher fluid surface of fluid 4 by means of the activated left probe 2 can be detected by an increase of the capacitance of the left probe 2, however, there is a further increase of the capacitance of the left probe 2 when the right probe 2' hits the liquid surface 10. Since it is difficult to discriminate between the increase of the capacitance C of the left probe 2 caused by hitting the fluid surface 10 and the increased of the capacitance C of the left probe 2 caused by the right probe 2' hitting the fluid surface 10 (both signal changes are positive), the higher fluid surface cannot be reliably detected.

While exemplary embodiments have been presented in the foregoing, it is to be understood that the embodiments are only examples, and are not intended to limit the scope, applicability, or configuration in any way. Obviously many modifications and variations of the present invention are possible in light of the above description. It is therefore to be understood, that within the scope of appended claims, the invention may be practiced otherwise than as specifically devised.

REFERENCE LIST

1 System
2, 2' Probe
3 Fluid vessel
4 Fluid
5 Fluid channel
6 Probe tip
7 Pump conduit
8 Work-plate
9 Moving mechanism
10 Fluid surface
11 System fluid
12 Pump
13 Transfer head
14 Transfer block
15 Block opening
16 Probe holder
17 Face side
18 Circuitry
19 Oscillator
20 Schmitt trigger circuit
21 Electric resistance R1 of the RC circuit
22, 22' Operational amplifier
23, 23' Input
24, 24' Output
25, 25' Coupling electrode
26 Controller
27 Shield signal circuit
28 Coaxial line
29 Electric conductor
30 Insulating layer
31 Conducting shield
32 Shield signal electrode
33, 33' Transistor
34 Collector contact
35 Emitter contact
36 Base contact
37 Connecting point
38 Signal detecting circuit
39 Signal generating circuit

The invention claimed is:

1. A method for detecting a fluid surface (10), comprising the following steps:
providing at least one probe (2) having an electric capacitance (C) with respect to its surroundings;
moving the probe (2) into or out of a fluid (4);
charging the probe (2) by applying a periodic first electric signal (S1) to the probe (2) for activating the probe (2);
applying a periodic third electric signal (S3) to one or more electrically conductive regions separate from the probe (2) simultaneously with applying the first electric signal (S1) to the probe (2), wherein the third electric signal (S3) is based on the first electric signal (S1);
at least partially discharging the probe (2) so as to obtain a discharging current;
detecting a second electric signal (S2) based on the discharging current;
analyzing the second electric signal (S2) or a signal derived from the second electric signal (S2) with respect to the capacitance (C) of the probe (2); and
identifying the fluid surface (10) of the fluid (4) based on a change of the capacitance (C) of the probe (2).

2. The method according to claim 1, wherein the third electric signal (S3) is applied to one or more probes (2) arranged adjacent to the activated probe (2).

3. The method according to claim 1, wherein the third electric signal (S3) is applied to one or more components of a moving system (9) for moving the activated probe (2) and/or one or more probes (2) arranged adjacent to the activated probe (2).

4. The method according to claim 1, wherein the third electric signal (S3) is applied to system fluid (11) of the activated probe (2) and/or one or more probes (2) arranged adjacent to the activated probe (2), the system fluid (11) being used for operating the probes (2) as pipettes.

5. The method according to claim 1, wherein the third electric signal (S3) is applied to a coaxial line (28) of the activated probe (2) and/or one or more probes (2) arranged adjacent to the activated probe (2).

6. The method according to claim 1, wherein the first electric signal (S1) is modulated by a fourth electric signal which periodically applies the first electric signal (S1) to the probe (2).

7. The method according to claim 6, wherein the first electric signal (S1) is sequentially applied to a respective one of a plurality of probes (2).

8. The method according to claim 1, wherein the third electric signal (S3) is derived from the first electric signal (S1).

9. The method according to claim 1, wherein the first electric signal (S1) is derived from the second electric signal (S2).

10. The method according to claim 1, wherein the first electric signal (S1) has a frequency in a range of from 1 kHz to 1 MHz.

11. An automated system (1) for detecting a fluid surface (10) of fluid (4) contained in a fluid vessel (3), comprising:
at least one probe (2, 2') having an electric capacitance (C) with respect to its surroundings;
a moving mechanism (9), adapted for moving the probe (2, 2') relative to fluid (4);
an electric circuitry (18), comprising:
a signal generating circuit (39) connected to the probe (2), configured to generate and apply a first electric signal (S1) to the probe (2) for charging the probe (2) so as to obtain an activated probe (2), an electric drain (19) for discharging the activated probe (2) to generate a discharging current, a controllable switch (33'), adapted to alternatively connect the probe (2) to the signal generating circuit (39) or to the drain, a signal detecting circuit (38) connected to the probe (2), configured to detect a second electric signal (S2) based on the discharging current of the probe (2), a shield signal circuit (27), adapted to apply a third electric signal (S3) being based on the first electric signal (S1) to one or more electrically conductive regions (2', 11, 16, 17, 28) separate from the probe (2); and a controller (26), set up to control detection of the fluid surface (10).

12. The system according to claim 11, wherein the controller (26) is set up to move the probe (2) into the fluid (4), to control the switch (33') to repeatedly charge and at least partially discharge the probe (2), to control the electric circuitry (18) to detect the second electric signal (18), to analyze the second electric signal (S2) or a signal derived from the second electric signal (S2) with respect to the capacitance (C) of the activated probe (2), to identify the fluid surface (10) of the fluid (4) based on a change of the capacitance (C) of the probe (2), wherein the third electric signal (S3) is applied to the one or more electrically conductive regions (2', 11, 16, 17, 28) different from the probe (2) simultaneously with applying the first electric signal (S1) to the probe (2).

13. The system according to claim 11, wherein the shield signal circuit (27) is electrically connected to one or more of the following electrically conductive regions:

one or more probes (2') arranged adjacent to the activated probe (2), one or more components of the moving system (9) for moving the activated probe (2) and/or one or more components of the moving system (9) for moving one or more probes (2') arranged adjacent to the activated probe (2), system fluid (11) of the activated probe (2) and/or system fluid (11) of one or more probes (2') arranged adjacent to the activated probe (2), a coaxial line (28) of the activated probe (2) and/or a coaxial line (28) of one or more probes (2') arranged adjacent to the activated probe (2).

14. The system according to claim 11, wherein the signal generating circuit (39) comprises a Schmitt trigger circuit (20) connected to a resistance-capacitance circuit, with the capacitance being provided by the activated probe (2).

15. The system according to claim 11, wherein the probe (2) is configured to perform pipetting operations for pipetting fluids.

\* \* \* \* \*